(12) United States Patent
Holmes et al.

(10) Patent No.: US 10,410,306 B1
(45) Date of Patent: *Sep. 10, 2019

(54) METHOD AND SYSTEM FOR PROVIDING REMOTE ACCESS TO DATA FOR DISPLAY ON A MOBILE DEVICE

(71) Applicant: Calgary Scientific Inc., Calgary (CA)

(72) Inventors: Colin J. Holmes, Vancouver, WA (US); Pierre Lemire, Calgary (CA); Glen Lehmann, Cremona (CA)

(73) Assignee: Calgary Scientific Inc., Calgary, AB (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/650,995

(22) Filed: Jul. 17, 2017

Related U.S. Application Data

(63) Continuation of application No. 13/343,105, filed on Jan. 4, 2012, now Pat. No. 9,741,084.

(Continued)

(51) Int. Cl.
  *G06F 15/173* (2006.01)
  *G06Q 50/22* (2018.01)
  *G06F 16/957* (2019.01)

(52) U.S. Cl.
  CPC ......... *G06Q 50/22* (2013.01); *G06F 16/9577* (2019.01)

(58) Field of Classification Search
  USPC .............. 709/225, 201, 202, 203, 227, 250
  See application file for complete search history.

(56) References Cited

U.S. PATENT DOCUMENTS

| | | |
|---|---|---|
| 4,975,690 A | 12/1990 | Torres |
| 5,249,121 A | 9/1993 | Baum |

(Continued)

FOREIGN PATENT DOCUMENTS

| | | |
|---|---|---|
| CA | 2646414 | 10/2007 |
| CA | 2697936 | 3/2009 |

(Continued)

OTHER PUBLICATIONS

ADASS XXI Conference Schedule, European Southern Observatory, http://www.eso.org/sci/meetings/2011/adass2011/program/schedule.html#day2, Nov. 7, 2011, 4 pages.

(Continued)

*Primary Examiner* — Lan Dai T Truong
(74) *Attorney, Agent, or Firm* — Meunier Carlin & Curfman LLC

(57) ABSTRACT

A method and system for providing remote access to data for display on a client computer via a computer network is provided. A first and second server computer connected to a computer network execute a first and second server remote access program, respectively, for communicating with an associated first and second application program. The client computer, which is also connected to the computer network, executes a client remote access program for simultaneously communicating with the first and second server remote access programs via a first and second communication link. The first and second server remote access programs determine first and second presentation data indicative of an application state of the first and second application programs. The client remote access program receives the first and the second presentation data and determines display data in dependence thereupon for substantially simultaneously displaying the first and the second presentation data.

20 Claims, 11 Drawing Sheets

Related U.S. Application Data

(60) Provisional application No. 61/429,655, filed on Jan. 4, 2011.

(56) References Cited

U.S. PATENT DOCUMENTS

| | | | |
|---|---|---|---|
| 5,345,550 A | 9/1994 | Bloomfield | |
| 5,491,800 A | 2/1996 | Goldsmith et al. | |
| 5,555,003 A | 9/1996 | Montgomery et al. | |
| 5,742,778 A | 4/1998 | Hao et al. | |
| 5,844,553 A | 12/1998 | Hao et al. | |
| 5,870,559 A * | 2/1999 | Leshem | G06F 11/32 |
| | | | 709/224 |
| 5,870,759 A | 2/1999 | Bauer et al. | |
| 5,903,725 A | 5/1999 | Colyer | |
| 5,909,545 A | 6/1999 | Frese, II et al. | |
| 5,920,311 A | 7/1999 | Anthias | |
| 5,978,842 A | 11/1999 | Noble et al. | |
| 5,987,376 A | 11/1999 | Olson et al. | |
| 5,996,002 A | 11/1999 | Katsurabayashi et al. | |
| 6,045,048 A | 4/2000 | Wilz et al. | |
| 6,061,689 A | 5/2000 | Chang et al. | |
| 6,075,531 A | 6/2000 | DeStefano | |
| 6,141,698 A | 10/2000 | Krishnan et al. | |
| 6,145,098 A | 11/2000 | Nouri et al. | |
| 6,151,621 A | 11/2000 | Colyer et al. | |
| 6,253,228 B1 | 6/2001 | Ferris et al. | |
| 6,342,906 B1 | 1/2002 | Kumar et al. | |
| 6,343,313 B1 | 1/2002 | Salesky et al. | |
| 6,453,334 B1 | 9/2002 | Vinson et al. | |
| 6,453,356 B1 | 9/2002 | Sheard et al. | |
| 6,529,230 B1 * | 3/2003 | Chong | G08B 25/14 |
| | | | 348/14.01 |
| 6,570,563 B1 | 5/2003 | Honda | |
| 6,601,233 B1 | 7/2003 | Underwood | |
| 6,602,185 B1 | 8/2003 | Uchikubo | |
| 6,662,210 B1 | 12/2003 | Carleton et al. | |
| 6,698,021 B1 | 2/2004 | Amini et al. | |
| 6,742,015 B1 | 5/2004 | Bowman-Amuah | |
| 6,748,418 B1 | 6/2004 | Yoshida et al. | |
| 6,763,371 B1 | 7/2004 | Jändel | |
| 6,792,607 B1 | 9/2004 | Burd et al. | |
| 6,918,113 B2 | 7/2005 | Patel et al. | |
| 6,938,096 B1 | 8/2005 | Greschler et al. | |
| 6,938,212 B2 | 8/2005 | Nakamura | |
| 6,970,459 B1 | 11/2005 | Meier | |
| 6,976,077 B1 | 12/2005 | Lehew et al. | |
| 6,981,062 B2 | 12/2005 | Suryanarayana | |
| 6,996,605 B2 | 2/2006 | Low et al. | |
| 7,003,550 B1 | 2/2006 | Cleasby et al. | |
| 7,065,568 B2 | 6/2006 | Bracewell et al. | |
| 7,069,227 B1 | 6/2006 | Lintel, III et al. | |
| 7,073,059 B2 | 7/2006 | Worely et al. | |
| 7,133,895 B1 | 11/2006 | Lee et al. | |
| 7,149,761 B2 | 12/2006 | Cooke et al. | |
| 7,152,092 B2 | 12/2006 | Beams et al. | |
| 7,167,893 B1 | 1/2007 | Malone et al. | |
| 7,174,504 B2 | 2/2007 | Tsao | |
| 7,181,686 B1 | 2/2007 | Bahrs | |
| 7,191,233 B2 | 3/2007 | Miller | |
| 7,193,985 B1 | 3/2007 | Lewis et al. | |
| 7,197,561 B1 | 3/2007 | Lovy et al. | |
| 7,240,162 B2 | 7/2007 | de Vries | |
| 7,246,063 B2 | 7/2007 | James et al. | |
| 7,254,634 B1 | 8/2007 | Davis et al. | |
| 7,287,054 B2 | 10/2007 | Lee et al. | |
| 7,320,131 B1 | 1/2008 | O'Toole, Jr. | |
| 7,343,310 B1 | 3/2008 | Stender | |
| 7,346,616 B2 | 3/2008 | Ramanujam et al. | |
| 7,350,151 B1 | 3/2008 | Nakajima | |
| 7,356,563 B1 | 4/2008 | Leichtling et al. | |
| 7,363,342 B1 | 4/2008 | Wang et al. | |
| 7,418,711 B1 | 8/2008 | Lee et al. | |
| 7,451,196 B1 | 11/2008 | de Vries et al. | |
| 7,533,146 B1 | 5/2009 | Kumar | |
| 7,577,751 B2 | 8/2009 | Vinson et al. | |
| 7,620,901 B2 | 11/2009 | Carpenter et al. | |
| 7,624,185 B2 | 11/2009 | Miller et al. | |
| 7,647,370 B1 | 1/2010 | Liu et al. | |
| 7,650,444 B2 | 1/2010 | Dirstine et al. | |
| 7,656,799 B2 | 2/2010 | Samuels et al. | |
| 7,676,506 B2 | 3/2010 | Reinsch | |
| 7,703,024 B2 | 4/2010 | Kautzleben et al. | |
| 7,706,399 B2 | 4/2010 | Janczak | |
| 7,725,331 B2 | 5/2010 | Schurenberg et al. | |
| 7,783,568 B1 | 8/2010 | Fracchia et al. | |
| 7,802,183 B1 | 9/2010 | Essin | |
| 7,810,089 B2 | 10/2010 | Sundarrajan et al. | |
| 7,831,919 B1 | 11/2010 | Viljoen et al. | |
| 7,921,078 B2 | 4/2011 | McCuller | |
| 7,941,488 B2 | 5/2011 | Goodman et al. | |
| 7,950,026 B1 | 5/2011 | Urbach | |
| 7,966,572 B2 | 6/2011 | Matthews et al. | |
| 7,984,115 B2 | 7/2011 | Tien et al. | |
| 8,010,901 B1 | 8/2011 | Rogers | |
| 8,024,523 B2 | 9/2011 | de Vries et al. | |
| 8,065,166 B2 | 11/2011 | Maresh et al. | |
| 8,122,341 B1 | 2/2012 | Dayan et al. | |
| 8,195,146 B2 | 6/2012 | Prakash et al. | |
| 8,239,773 B1 | 8/2012 | Billman | |
| 8,261,345 B2 | 9/2012 | Hitomi et al. | |
| 8,356,252 B2 | 1/2013 | Raman et al. | |
| 8,359,591 B2 | 1/2013 | de Vries et al. | |
| 8,478,307 B1 | 7/2013 | Hayes | |
| 8,509,230 B2 | 8/2013 | Vinson et al. | |
| 8,527,591 B2 | 9/2013 | Pirnazar | |
| 8,527,706 B2 | 9/2013 | de Vries et al. | |
| 8,533,103 B1 | 9/2013 | Certain et al. | |
| 8,572,178 B1 | 10/2013 | Frazzini et al. | |
| 8,606,952 B2 | 12/2013 | Pasetto et al. | |
| 8,607,158 B2 | 12/2013 | Molander et al. | |
| 8,627,081 B2 | 1/2014 | Grimen et al. | |
| 8,667,054 B2 | 3/2014 | Tahan | |
| 8,799,354 B2 | 8/2014 | Thomas et al. | |
| 8,832,260 B2 | 9/2014 | Raja et al. | |
| 8,856,259 B2 | 10/2014 | Burckart et al. | |
| 8,909,703 B2 | 12/2014 | Gupta et al. | |
| 8,910,112 B2 | 12/2014 | Li et al. | |
| 8,924,512 B2 | 12/2014 | Stoyanov et al. | |
| 8,935,328 B2 | 1/2015 | Tumuluri | |
| 9,152,970 B1 | 10/2015 | Trahan | |
| 9,239,812 B1 | 1/2016 | Berlin | |
| 9,256,856 B1 | 2/2016 | Fairs et al. | |
| 9,686,205 B2 | 6/2017 | Leitch et al. | |
| 2001/0006382 A1 * | 7/2001 | Sevat | H04N 5/44591 |
| | | | 345/169 |
| 2001/0033299 A1 | 10/2001 | Callaway et al. | |
| 2001/0037358 A1 | 11/2001 | Clubb et al. | |
| 2001/0047393 A1 | 11/2001 | Arner et al. | |
| 2002/0032751 A1 | 3/2002 | Bharadwaj | |
| 2002/0032783 A1 | 3/2002 | Tuatini | |
| 2002/0032804 A1 | 3/2002 | Hunt | |
| 2002/0051541 A1 | 5/2002 | Glick et al. | |
| 2002/0092029 A1 | 7/2002 | Smith | |
| 2002/0198941 A1 | 12/2002 | Gavrilescu et al. | |
| 2003/0014735 A1 | 1/2003 | Achlioptas et al. | |
| 2003/0023670 A1 | 1/2003 | Walrath | |
| 2003/0055893 A1 | 3/2003 | Sato et al. | |
| 2003/0065738 A1 | 4/2003 | Yang et al. | |
| 2003/0120324 A1 | 6/2003 | Osborn et al. | |
| 2003/0120762 A1 | 6/2003 | Yepishin et al. | |
| 2003/0149721 A1 | 8/2003 | Alfonso-Nogueiro et al. | |
| 2003/0149941 A1 | 8/2003 | Tsao | |
| 2003/0163514 A1 | 8/2003 | Waldschmidt | |
| 2003/0179230 A1 | 9/2003 | Seidman | |
| 2003/0184584 A1 | 10/2003 | Vachuska et al. | |
| 2003/0208472 A1 | 11/2003 | Pham | |
| 2004/0015842 A1 | 1/2004 | Nanivadekar et al. | |
| 2004/0029638 A1 | 2/2004 | Hytcheson et al. | |
| 2004/0039742 A1 | 2/2004 | Barsness et al. | |
| 2004/0045017 A1 | 3/2004 | Dorner et al. | |
| 2004/0068516 A1 | 4/2004 | Lee et al. | |
| 2004/0077347 A1 | 4/2004 | Lauber et al. | |
| 2004/0103195 A1 | 5/2004 | Chalasani et al. | |

(56) References Cited

U.S. PATENT DOCUMENTS

| | | |
|---|---|---|
| 2004/0103339 A1 | 5/2004 | Chalasani et al. |
| 2004/0106916 A1 | 6/2004 | Quaid et al. |
| 2004/0117804 A1 | 6/2004 | Scahill et al. |
| 2004/0128354 A1 | 7/2004 | Horikiri et al. |
| 2004/0153525 A1 | 8/2004 | Borella |
| 2004/0162876 A1 | 8/2004 | Kohavi |
| 2004/0183827 A1 | 9/2004 | Putterman et al. |
| 2004/0225960 A1 | 11/2004 | Parikh et al. |
| 2004/0236633 A1 | 11/2004 | Knauerhase et al. |
| 2004/0243919 A1 | 12/2004 | Muresan et al. |
| 2004/0249885 A1 | 12/2004 | Petropoulakis et al. |
| 2005/0005024 A1 | 1/2005 | Samuels et al. |
| 2005/0010871 A1 | 1/2005 | Ruthfield et al. |
| 2005/0021687 A1 | 1/2005 | Anastassopoulos et al. |
| 2005/0050229 A1 | 3/2005 | Comeau et al. |
| 2005/0114711 A1 | 5/2005 | Hesselink et al. |
| 2005/0114789 A1 | 5/2005 | Chang et al. |
| 2005/0138631 A1 | 6/2005 | Bellotti et al. |
| 2005/0154288 A1 | 7/2005 | Wang |
| 2005/0188046 A1 | 8/2005 | Hickman et al. |
| 2005/0188313 A1 | 8/2005 | Matthews et al. |
| 2005/0190203 A1 | 9/2005 | Gery et al. |
| 2005/0193062 A1 | 9/2005 | Komine et al. |
| 2005/0198578 A1 | 9/2005 | Agrawala et al. |
| 2005/0216421 A1 | 9/2005 | Barry et al. |
| 2005/0240906 A1 | 10/2005 | Kinderknecht et al. |
| 2005/0246422 A1 | 11/2005 | Laning |
| 2006/0004874 A1 | 1/2006 | Hutcheson et al. |
| 2006/0026006 A1 | 2/2006 | Hindle |
| 2006/0031377 A1 | 2/2006 | Ng et al. |
| 2006/0031481 A1 | 2/2006 | Patrick et al. |
| 2006/0036770 A1 | 2/2006 | Hosn et al. |
| 2006/0041686 A1 | 2/2006 | Caspi et al. |
| 2006/0041891 A1 | 2/2006 | Aaron |
| 2006/0053380 A1 | 3/2006 | Spataro et al. |
| 2006/0066717 A1 | 3/2006 | Miceli |
| 2006/0069797 A1 | 3/2006 | Abdo et al. |
| 2006/0085245 A1 | 4/2006 | Takatsuka et al. |
| 2006/0085835 A1 | 4/2006 | Istvan et al. |
| 2006/0101397 A1 | 5/2006 | Mercer et al. |
| 2006/0112188 A1 | 5/2006 | Albanese et al. |
| 2006/0130069 A1 | 6/2006 | Srinivasan et al. |
| 2006/0179119 A1 | 8/2006 | Kurosawa et al. |
| 2006/0221081 A1 | 10/2006 | Cohen et al. |
| 2006/0231175 A1 | 10/2006 | Vondracek et al. |
| 2006/0236328 A1 | 10/2006 | DeWitt |
| 2006/0242254 A1 | 10/2006 | Okazaki et al. |
| 2006/0258462 A1 | 11/2006 | Cheng et al. |
| 2006/0265689 A1 | 11/2006 | Kuznetsov et al. |
| 2006/0271563 A1 | 11/2006 | Angelo et al. |
| 2006/0288171 A1 | 12/2006 | Tsien |
| 2006/0294418 A1 | 12/2006 | Fuchs |
| 2007/0024645 A1 | 2/2007 | Purcell et al. |
| 2007/0024706 A1 | 2/2007 | Brannon et al. |
| 2007/0047535 A1 | 3/2007 | Varma |
| 2007/0067754 A1 | 3/2007 | Chen et al. |
| 2007/0079244 A1 | 4/2007 | Brugiolo |
| 2007/0112880 A1 | 5/2007 | Yang et al. |
| 2007/0120763 A1* | 5/2007 | De Paepe ........... G06F 3/03547 345/1.3 |
| 2007/0130292 A1 | 6/2007 | Tzruya et al. |
| 2007/0143398 A1 | 6/2007 | Graham |
| 2007/0203944 A1 | 8/2007 | Batra et al. |
| 2007/0203990 A1 | 8/2007 | Townsley et al. |
| 2007/0203999 A1 | 8/2007 | Townsley et al. |
| 2007/0208718 A1 | 9/2007 | Javid et al. |
| 2007/0226636 A1 | 9/2007 | Carpenter et al. |
| 2007/0233706 A1 | 10/2007 | Farber et al. |
| 2007/0244930 A1 | 10/2007 | Bartlette et al. |
| 2007/0244962 A1 | 10/2007 | Laadan et al. |
| 2007/0244990 A1 | 10/2007 | Wells |
| 2007/0256073 A1 | 11/2007 | Truong et al. |
| 2007/0282951 A1 | 12/2007 | Selimis et al. |
| 2008/0016155 A1 | 1/2008 | Khalatian |
| 2008/0028323 A1 | 1/2008 | Rosen et al. |
| 2008/0052377 A1 | 2/2008 | Light |
| 2008/0134211 A1 | 6/2008 | Cui |
| 2008/0146194 A1 | 6/2008 | Yang et al. |
| 2008/0159175 A1 | 7/2008 | Flack |
| 2008/0183190 A1 | 7/2008 | Adcox et al. |
| 2008/0195362 A1 | 8/2008 | Belcher et al. |
| 2008/0276183 A1 | 11/2008 | Siegrist et al. |
| 2008/0301228 A1 | 12/2008 | Flavin |
| 2008/0313282 A1 | 12/2008 | Warila et al. |
| 2008/0320081 A1 | 12/2008 | Shriver-Blake et al. |
| 2009/0070404 A1 | 3/2009 | Mazzaferri |
| 2009/0080523 A1 | 3/2009 | McDowell |
| 2009/0089742 A1 | 4/2009 | Nagulu et al. |
| 2009/0094369 A1 | 4/2009 | Woolbridge et al. |
| 2009/0106422 A1 | 4/2009 | Kriewall |
| 2009/0119644 A1 | 5/2009 | de Vries et al. |
| 2009/0164581 A1 | 6/2009 | Bove et al. |
| 2009/0172100 A1 | 7/2009 | Callanan et al. |
| 2009/0187817 A1 | 7/2009 | Ivashin et al. |
| 2009/0209239 A1 | 8/2009 | Montesdeoca |
| 2009/0217177 A1 | 8/2009 | DeGrazia |
| 2009/0044171 A1 | 12/2009 | Avadhanula |
| 2009/0328032 A1 | 12/2009 | Crow et al. |
| 2010/0012911 A1* | 1/2010 | Akinaga ................. H01L 45/04 257/2 |
| 2010/0017727 A1 | 1/2010 | Offer et al. |
| 2010/0018827 A1 | 1/2010 | Ueda |
| 2010/0061238 A1 | 3/2010 | Godbole et al. |
| 2010/0077058 A1 | 3/2010 | Messer |
| 2010/0082747 A1 | 4/2010 | Yue et al. |
| 2010/0115023 A1 | 5/2010 | Peled |
| 2010/0131591 A1 | 5/2010 | Thomas et al. |
| 2010/0150031 A1 | 6/2010 | Allen et al. |
| 2010/0174773 A1 | 7/2010 | Penner et al. |
| 2010/0205147 A1 | 8/2010 | Lee |
| 2010/0223566 A1 | 9/2010 | Holmes et al. |
| 2010/0223661 A1 | 9/2010 | Yang |
| 2010/0268762 A1 | 10/2010 | Pahlavan et al. |
| 2010/0268813 A1 | 10/2010 | Pahlavan et al. |
| 2010/0274858 A1 | 10/2010 | Lindberg et al. |
| 2010/0281107 A1 | 11/2010 | Fallows et al. |
| 2010/0306642 A1 | 12/2010 | Lowet |
| 2011/0047190 A1 | 2/2011 | Lee et al. |
| 2011/0058052 A1 | 3/2011 | Bolton |
| 2011/0113350 A1 | 5/2011 | Carlos et al. |
| 2011/0119716 A1 | 5/2011 | Coleman, Sr. |
| 2011/0128378 A1 | 6/2011 | Raji |
| 2011/0138016 A1 | 6/2011 | Jung et al. |
| 2011/0138283 A1 | 6/2011 | Marston |
| 2011/0145863 A1 | 6/2011 | Alsina et al. |
| 2011/0154302 A1 | 6/2011 | Balko et al. |
| 2011/0154464 A1 | 6/2011 | Agarwal et al. |
| 2011/0157196 A1 | 6/2011 | Nave et al. |
| 2011/0162062 A1 | 6/2011 | Kumar et al. |
| 2011/0184993 A1 | 7/2011 | Chawla et al. |
| 2011/0187652 A1 | 8/2011 | Huibers |
| 2011/0191438 A1 | 8/2011 | Huibers et al. |
| 2011/0191823 A1 | 8/2011 | Huibers |
| 2011/0213830 A1 | 9/2011 | Lopez et al. |
| 2011/0219419 A1 | 9/2011 | Reisman |
| 2011/0222442 A1 | 9/2011 | Cole et al. |
| 2011/0223882 A1 | 9/2011 | Hellgren |
| 2011/0246991 A1 | 10/2011 | Schubert et al. |
| 2011/0252152 A1 | 10/2011 | Sherry et al. |
| 2011/0314093 A1 | 12/2011 | Sheu et al. |
| 2012/0023418 A1 | 1/2012 | Frields et al. |
| 2012/0030275 A1 | 2/2012 | Boller et al. |
| 2012/0072833 A1 | 3/2012 | Song et al. |
| 2012/0072835 A1* | 3/2012 | Gross ................... G06Q 10/10 715/243 |
| 2012/0079080 A1 | 3/2012 | Pishevar |
| 2012/0079111 A1* | 3/2012 | Luukkala .............. H04W 76/45 709/225 |
| 2012/0084713 A1 | 4/2012 | Desai et al. |
| 2012/0090004 A1 | 4/2012 | Jeong |
| 2012/0133675 A1 | 5/2012 | McDowell |
| 2012/0151373 A1 | 6/2012 | Kominac et al. |
| 2012/0154633 A1 | 6/2012 | Rodriguez |
| 2012/0159308 A1 | 6/2012 | Tseng et al. |

(56) References Cited

U.S. PATENT DOCUMENTS

| | | |
|---|---|---|
| 2012/0159356 A1 | 6/2012 | Steelberg |
| 2012/0169874 A1 | 7/2012 | Thomas et al. |
| 2012/0210242 A1 | 8/2012 | Burckart et al. |
| 2012/0210243 A1 | 8/2012 | Uhma et al. |
| 2012/0221792 A1 | 8/2012 | de Vries et al. |
| 2012/0226742 A1 | 9/2012 | Momchilov et al. |
| 2012/0233555 A1 | 9/2012 | Psistakis et al. |
| 2012/0245918 A1 | 9/2012 | Overton et al. |
| 2012/0246225 A1 | 9/2012 | Lemire et al. |
| 2012/0324032 A1 | 12/2012 | Chan |
| 2012/0324358 A1 | 12/2012 | Jooste |
| 2012/0331061 A1 | 12/2012 | Lininger |
| 2013/0007227 A1 | 1/2013 | Hitomi et al. |
| 2013/0013671 A1 | 1/2013 | Relan et al. |
| 2013/0031618 A1 | 1/2013 | Momchilov |
| 2013/0046815 A1 | 2/2013 | Thomas et al. |
| 2013/0046816 A1 | 2/2013 | Thomas et al. |
| 2013/0054679 A1 | 2/2013 | Jooste |
| 2013/0070740 A1 | 3/2013 | Yovin |
| 2013/0086155 A1 | 4/2013 | Thomas et al. |
| 2013/0086156 A1 | 4/2013 | McFadzean et al. |
| 2013/0086652 A1 | 4/2013 | Kavantzas et al. |
| 2013/0110895 A1 | 5/2013 | Valentino et al. |
| 2013/0113833 A1 | 5/2013 | Larsson |
| 2013/0117474 A1 | 5/2013 | Ajanovic et al. |
| 2013/0120368 A1 | 5/2013 | Miller |
| 2013/0132485 A1 | 5/2013 | Thomas et al. |
| 2013/0138791 A1 | 5/2013 | Thomas et al. |
| 2013/0147845 A1 | 6/2013 | Xie et al. |
| 2013/0159062 A1 | 6/2013 | Stiehl |
| 2013/0159709 A1 | 6/2013 | Ivory et al. |
| 2013/0179962 A1 | 7/2013 | Arai et al. |
| 2013/0208966 A1 | 8/2013 | Zhao et al. |
| 2013/0212483 A1 | 8/2013 | Brakensiek et al. |
| 2013/0262566 A1 | 10/2013 | Stephure et al. |
| 2013/0297676 A1 | 11/2013 | Binyamin |
| 2013/0346482 A1 | 12/2013 | Holmes |
| 2014/0053085 A1 | 2/2014 | Stephure et al. |
| 2014/0136667 A1 | 5/2014 | Gonsalves et al. |
| 2014/0207858 A1 | 7/2014 | Thomas et al. |
| 2014/0240524 A1 | 8/2014 | Julia et al. |
| 2014/0241229 A1 | 8/2014 | Bertorelle et al. |
| 2014/0258441 A1 | 9/2014 | L'Heureux et al. |
| 2014/0298420 A1 | 10/2014 | Barton et al. |
| 2015/0026338 A1 | 1/2015 | Lehmann et al. |
| 2015/0067769 A1 | 3/2015 | Barton et al. |
| 2015/0156133 A1 | 6/2015 | Leitch et al. |
| 2015/0319252 A1 | 11/2015 | Momchilov et al. |
| 2016/0054897 A1 | 2/2016 | Holmes et al. |
| 2016/0226979 A1 | 8/2016 | Lancaster et al. |
| 2017/0228799 A1* | 8/2017 | Perry ................. G06Q 30/0277 |

FOREIGN PATENT DOCUMENTS

| | | |
|---|---|---|
| CA | 2742779 | 6/2010 |
| CN | 1278623 | 1/2001 |
| CN | 1499841 | 5/2004 |
| CN | 101539932 | 9/2009 |
| CN | 102129632 | 7/2011 |
| CN | 102821413 | 12/2012 |
| EP | 0349463 | 1/1990 |
| EP | 1422901 | 5/2004 |
| JP | 2007/084744 | 3/1995 |
| JP | 2002/055870 | 2/2002 |
| JP | 2004/206363 | 7/2004 |
| JP | 2004/287758 | 10/2004 |
| JP | 2005/031807 | 2/2005 |
| JP | 2005/521946 | 7/2005 |
| JP | 2008/099055 | 4/2008 |
| JP | 2010/256972 | 11/2010 |
| RU | 2295752 | 3/2007 |
| RU | 2298287 | 4/2007 |
| RU | 2305860 | 9/2007 |
| WO | 1998/025666 | 6/1998 |
| WO | 1998/058478 | 12/1998 |
| WO | 2001/016724 | 3/2001 |
| WO | 2001/091482 | 11/2001 |
| WO | 2002/009106 | 1/2002 |
| WO | 2003/032569 | 4/2003 |
| WO | 2003/083684 | 10/2003 |
| WO | 2008/011063 | 1/2008 |
| WO | 2008/087636 | 7/2008 |
| WO | 2010/060206 | 6/2010 |
| WO | 2010/088768 | 8/2010 |
| WO | 2010/127327 | 11/2010 |
| WO | 2011/087545 | 7/2011 |
| WO | 2012/093330 | 7/2012 |
| WO | 2012/127308 | 9/2012 |
| WO | 2013/024342 | 2/2013 |
| WO | 2013/024343 | 2/2013 |
| WO | 2013/046015 | 4/2013 |
| WO | 2013/046016 | 4/2013 |
| WO | 2013/072764 | 5/2013 |
| WO | 2013/109984 | 7/2013 |
| WO | 2013/128284 | 9/2013 |
| WO | 2013/153439 | 10/2013 |
| WO | 2014/033554 | 3/2014 |
| WO | 2015/080845 | 6/2015 |

OTHER PUBLICATIONS

Brandom, R., "Google Photos and the unguessable URL," The Verge, retrieved on Sep. 25, 2017 from https://www.theverg.com/2015/6/23/8830977/google-photos-security-public-url-privacy-protected, Jun. 23, 2015, 7 pages.

"Calgary Scientific Revolutionizes Application Sharing and Advanced Collaboration with PureWeb 3.0," Press Release, Jun. 21, 2011, 3 pages.

Coffman, Daniel, et al., "A Client-Server Architecture for State-Dependent Dynamic Visualizations on the Web," IBM T.J. Watson Research Center, 2010, 10 pages.

Federl, P., "Remote Visualization of Large Multi-dimensional Radio Astronomy Data Sets," Institute for Space Imaging Science, University of Calgary, 2012, pp. 1-10.

Federl, P., "Remote Visualization of Large Multi-dimensional Radio Astronomy Data Sets," Institute for Space Imaging Science, University of Calgary, 2012, pp. 11-22.

Fraser, N., "Differential Synchronization," Google, Mountain View, CA, Jan. 2009, 8 pages.

GoInstant, Shared Browsing Technology, http://website.s3.goinstant.com.s3.amazonaws.com/wp-content/uploads/2012/04/GoInstant-Shared-Web-Technology.pdf, 2012, 4 pages.

"GTK 3, Broadway and an HTML5 websocket gui, for free," retrieved on Sep. 26, 2017 at http://compsci.ca/v3/viewtopic.php?t=36823, Apr. 12, 2014, pp. 1-3.

Hong, C., et al., "Multimedia Presentation Authoring and Virtual Collaboration in Medicine," International Journal of Kimics, vol. 8, No. 6, 2010, pp. 690-696.

Jourdain, Sebastien, et al., "ParaViewWeb: A Web Framework for 3D Visualization and Data Processing," International Journal of Computer Information Systems and Industrial Management Applications, vol. 3, 2011, pp. 870-877.

Layers: Capture Every Item on Your Screen as a PSD Layered Image, Internet Website, retrieved on Jun. 30, 2016 at http://web.archive.org/web/20140218111143, 2014, 9 pages.

Li, S.F., et al., "Integrating Synchronous and Asynchronous Collaboration with Virtual Network Computing," Internet Computing, IEEE 4.3, 2000, pp. 26-33.

Luo, Y., et al., "Real Time Multi-User Interaction with 3D Graphics via Communication Networks," 1998 IEEE Conference on Information Visualization, 1998, 9 pages.

Microsoft Computer Dictionary, Microsoft Press, 5$^{th}$ Edition, Mar. 15, 2002, p. 624.

Mitchell, J. Ross, et al., A Smartphone Client-Server Teleradiology System for Primary Diagnosis of Acute Stroke, Journal of Medical Internet Research, vol. 13, Issue 2, 2011, 12 pages.

ParaViewWeb, KitwarePublic, retrieved on Jan. 27, 2014 from http://www.paraview.org/Wiki/ParoViewWeb, 1 page.

(56) References Cited

OTHER PUBLICATIONS

Remote Desktop Protocol (RDP), retrieved on May 4, 2014 from http://en.wikipedia.org/wiki/Remote_Desktop_Protocol, 7 pages.
Remote Desktop Services (RDS), Remote App, retrieved on May 4, 2014 from http://en.wikipedia.org/wiki/Remote_Desktop_Services, 9 pages.
Remote Desktop Services (RDS), Windows Desktop Sharing, retrieved on May 4, 2014 from http://en.wikipedia.org/wiki/Remote_Desktop_Services, 9 pages.
Samesurf web real-time co-browser application, http://i.samesurf.com/i/0586021, 2009, 2 pages.
Shim, H., et al., Providing Flexible Services for Managing Shared State in Collaborative Systems, Proceedings of the Fifth European Conference, 1997, pp. 237-252.
Yang, L., et al., "Multirate Control in Internet-Based Control Systems," IEEE Transactions on Systems, Man, and Cybernetics: Part C: Applications and Reviews, vol. 37, No. 2, 2007, pp. 185-192.

* cited by examiner

METHOD AND SYSTEM FOR PROVIDING REMOTE ACCESS TO DATA FOR DISPLAY ON A MOBILE DEVICE

CROSS-REFERENCE TO RELATED APPLICATION

This application is a continuation of U.S. patent application Ser. No. 13/343,105, filed Jan. 4, 2012, entitled "Method and System for Providing Remote Access to Data for Display on a Mobile Device." This application also claims priority to U.S. Patent Application No. 61/429,655, entitled, "Method and System for Providing Remote Access to Data for Display on a Mobile Device," filed Jan. 4, 2011. The above-referenced applications are incorporated herein by reference in their entireties.

BACKGROUND OF THE DISCLOSURE

In numerous present day scenarios, computer networks may provide remote access to data for display on a mobile device, and in particular to enable remote access to data that are stored in different locations. For example, in the healthcare sector a medical practitioner, such as a surgeon working at a first hospital, may want to compare medical imaging data, such as, for example, MRI data or CT Scan data of a patient captured at the first hospital with imaging data of the patient that have been previously captured at a second hospital or medical imaging facility. In another example, a medical practitioner may want to compare imaging data captured of a patient with reference imaging data stored in a medical repository.

Use of wireless handheld devices such as, for example, IPHONE, ANDROID, and IPAD has rapidly increased over the last couple of years to the extent that now nearly every professional owns at least one wireless handheld device. State of the art wireless mobile technology enables use of small wireless handheld devices to access the Internet and download various forms of image data files for display thereon.

SUMMARY OF THE DISCLOSURE

A method and system for providing remote access to data for display on a device such as a mobile device via a computer network is provided. According to some implementations, the method and system provide substantially simultaneous remote access to data stored in different locations for display on a wireless handheld device via a wireless computer network.

According to some implementations, there are disclosed methods of providing remote access to a plurality of application programs executing on plural server computers. The methods include providing at least one server remote access program on each the plural server computers, each of the plural server remote access programs being in communication with a respective one of plural application programs; providing at least one remote connection to a client remote access program executing on a client computer, the at least one remote connection enabling remote access to the plural application programs, and the client remote access program communicating with the at least one server remote access program over the at least one remote connection; communicating presentation data representing a change in a state of at least one of the plural application programs to the client remote access program; and displaying the presentation data at the client computer.

According to some implementations, there are disclosed methods of providing remote access to a plurality of application programs executing on plural server computers. The methods may include providing a server remote access program on each of the plural server computers, each server remote access program being in communication with a respective one of plural application programs; providing at least one remote connection to a client remote access program executing on a client computer, the at least one remote connection enabling remote access to the plural application programs; and communicating presentation data representing a change in a state of at least one of the plural application programs to the client remote access program.

According to some implementations, there are disclosed methods of providing remote access to a plurality of application programs executing at a client computer. The methods may include providing a client remote access program on the client computer, the client remote access program being in communication with plural server computers, each of the plural server computers executing a server remote access program that is in communication with a respective one of the plural application programs; making remote connections to each server remote access program, the remote connections enabling remote access to the plural application programs; communicating presentation data representing a change in a state of the plural application programs to the client remote access program; and displaying the presentation data at the client computer.

These and other objects and advantages may be provided by the embodiments of the disclosure, including some implementations exemplified in the description and figures.

BRIEF DESCRIPTION OF THE DRAWINGS

The accompanying drawings, which are incorporated in and constitute a part of this disclosure, illustrate various implementations. Like reference numerals are used to reference like elements throughout. In the drawings.

DETAILED DESCRIPTION OF THE DISCLOSURE

Unless defined otherwise, all technical and scientific terms used herein have the same meaning as commonly understood by one of ordinary skill in the art. While implementations of the disclosure will be described for providing substantially simultaneous remote access to imaging data stored in two different locations in a clinical environment for display on a wireless handheld device only for the sake of simplicity, it will become evident to those skilled in the art that the embodiments of the disclosure are not limited thereto, but are applicable for providing remotes access to any number of locations, various other forms of data, in numerous other present day applications, and for display on other devices such as laptop computers or personal computers.

Figure 1:
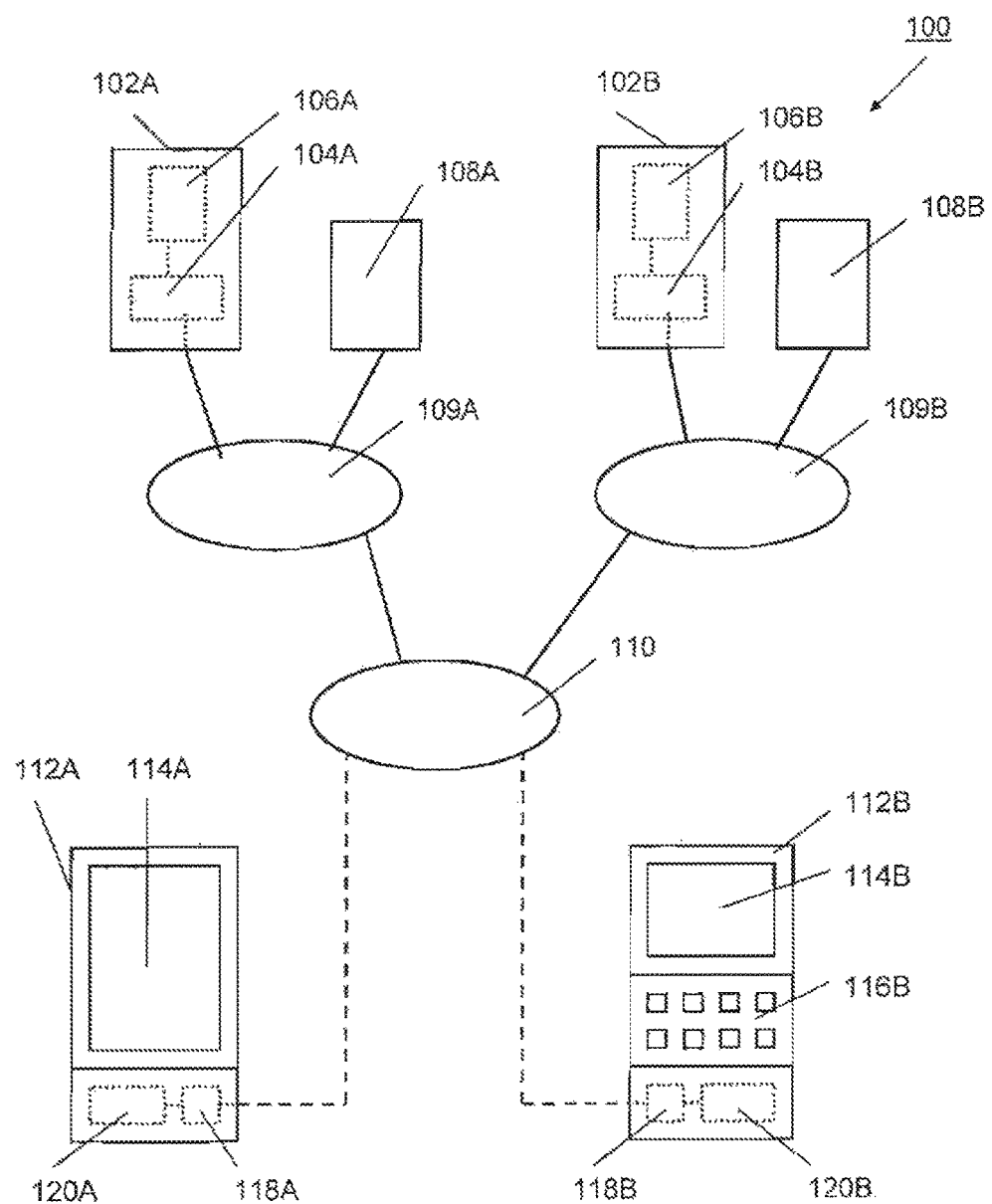
FIG. 1 is a simplified block diagram of a system for providing remote access to data for display on a mobile device via a computer network.

Referring to FIG. 1, a system 100 for providing remote access to data for display on a mobile device via a computer network according to the present disclosure is shown. The system comprises a client computer 112A or 112B, such as wireless handheld device such as, for example, an IPHONE 112A or a BLACKBERRY 112B connected via a communication network 110 such as, for example, the Internet, to a first server computer 102A and a second server computer 102B. Other client computers may be connected to the communication network 110, such as desktop computers, laptop/notebook computers, thin client devices, virtual computers, etc., that are either wired or wirelessly connected to the communication network 110.

The first server computer 102A may be connected to a first Local Area Network (LAN) 109A of a first hospital while the second server computer 102B is connected to a second Local Area Network (LAN) 109B of a second hospital. Imaging data such as, for example, MRI imaging data, CT Scan imaging data and X-ray imaging data captured at the first and the second hospital are stored in data bases 108A and 108B connected to the LANs 109A and 109B, respectively. Typically, the server computers 102A and 102B execute an electronic Picture Archiving and Communication System (PACS) using the Digital Imaging and Communications in Medicine (DICOM) format for storage and transfer. As is evident to those skilled in the art, the DICOM format is substantially unsuitable for providing remote access thereto and for displaying the same on a wireless handheld device. The PACS or other image retrieval or image processing application programs are performed, for example, by executing on the processors 104A and 104B executable commands of the respective application programs stored in memory 106A and 106B of the server computers 102A and 102B.

According to some implementations, access to data using, for example, a handheld wireless device 112A, 112B is enabled by executing: a first server remote access program on the processor 104A of the first server computer 102A; a second server remote access program on the processor 104B of the second server computer 102B; and a respective client remote access program executed on a processor 118A, 118B of the client computer 112A, 112B. The first and the second server remote access program may be performed by executing executable commands stored in the memory 106A and 106B of the first and the second server computer 102A and 102B while the client remote access program is performed by executing executable commands stored in memory 120A, 120B of the client computer 112A, 112B. An example of the server remote access program is PUREWEB, available from Calgary Scientific, Inc. of Calgary, Alberta.

Figure 2:
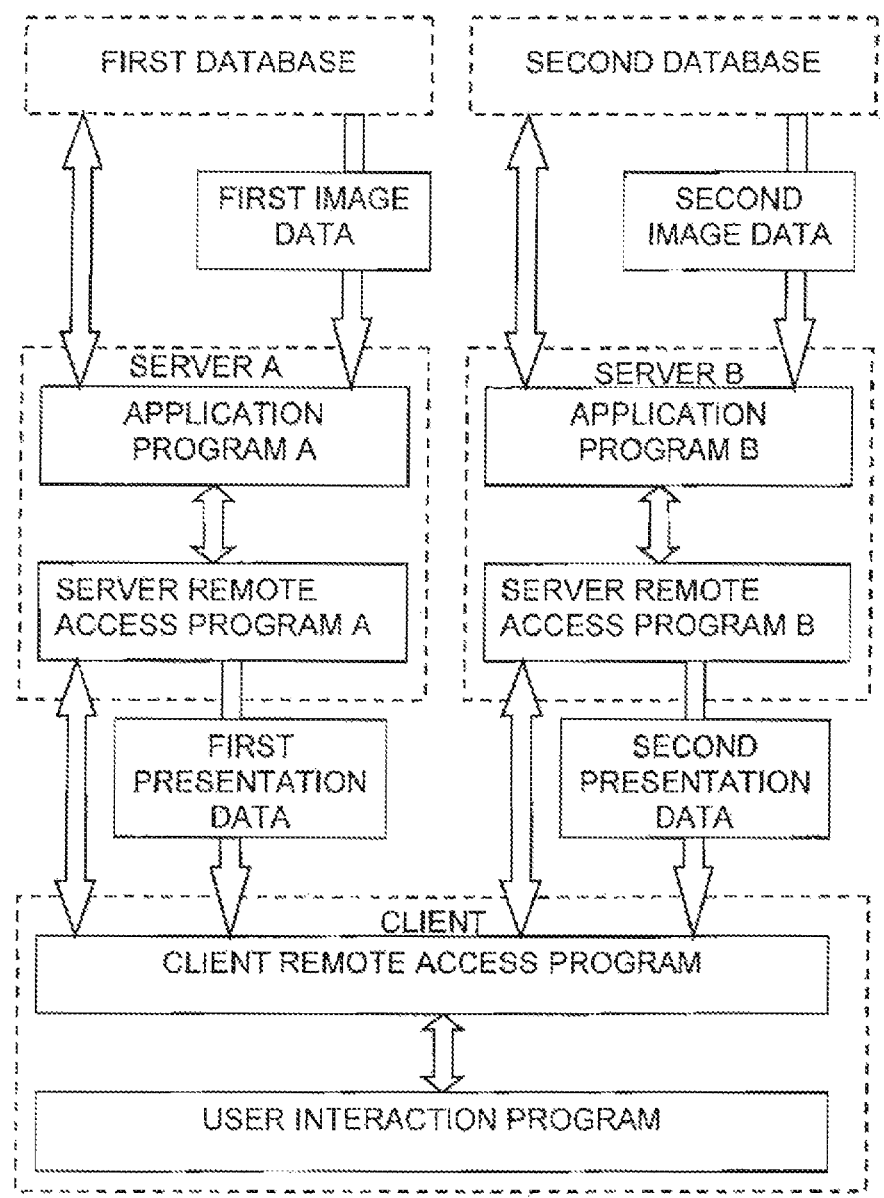
FIG. 2 is a simplified block diagram illustrating communication of a client computer with a first server computer and a second server computer of the system shown in FIG. 1.

As illustrated in FIG. 2, communication between the client computer 112A or 112B and the first and second server computer 102A and 102B is provided as communication between the first and the second server remote access program and the client remote access program via, for example, a wireless computer network. The first and the second server remote access program communicate with a respective first and second application program such as, for example, a PACS program. The first and the second application program communicate with the respective databases 108A and 108B for retrieving respective first and second image data therefrom. The client remote access program communicates with a user interaction program such as, for example, a web browser for displaying data such as, for example, image data and image processing control data; for receiving user input data for interacting with the first and the second application program using, for example, a graphical display with touch-screen 114A or a graphical display 114B and a keyboard 116B or the handheld wireless device 112A, 112B, respectively.

The first and the second server remote access program and the client remote access program may be implemented using standard programming languages and communication is enabled using standard communication technologies such as, for example, Hyper Text Transfer Protocol (HTTP), virtual private networks (VPN), and secure socket layers (SSL), which are well known to those skilled in the art. Provision of the first and the second server remote access program and the client remote access program enable implementation of aspects of the disclosure as a retrofit to existing technologies on the server side as well as on the client side.

The first and the second server remote access program receive first and second image data from the first and the second application program, respectively. Upon receipt, the first and the second server remote access program generate first and second "presentation data" of the first and second image data and transmit the same to the client remote access program. The first and second presentation data may be generated in a fashion according to hardware capabilities of the client computer 112A, 1128, for example, in accordance with processing capacity, memory size, type of graphical display, and type of user interface.

For example, presentation data generated and transmitted for a laptop computer or desktop computer are different from presentation data generated and transmitted for a handheld device such as, for example, an IPHONE. Generation of presentation data enables a substantial reduction in the amount of data transmitted for display on the small display of a handheld wireless device, i.e., results in a reduction in bandwidth utilization. Furthermore, the generation of presentation data addresses safety or privacy issues related to sensitive data such as medical imaging data by obviating the transmission of the sensitive data from the server computer to the client computer.

Figure 3A:
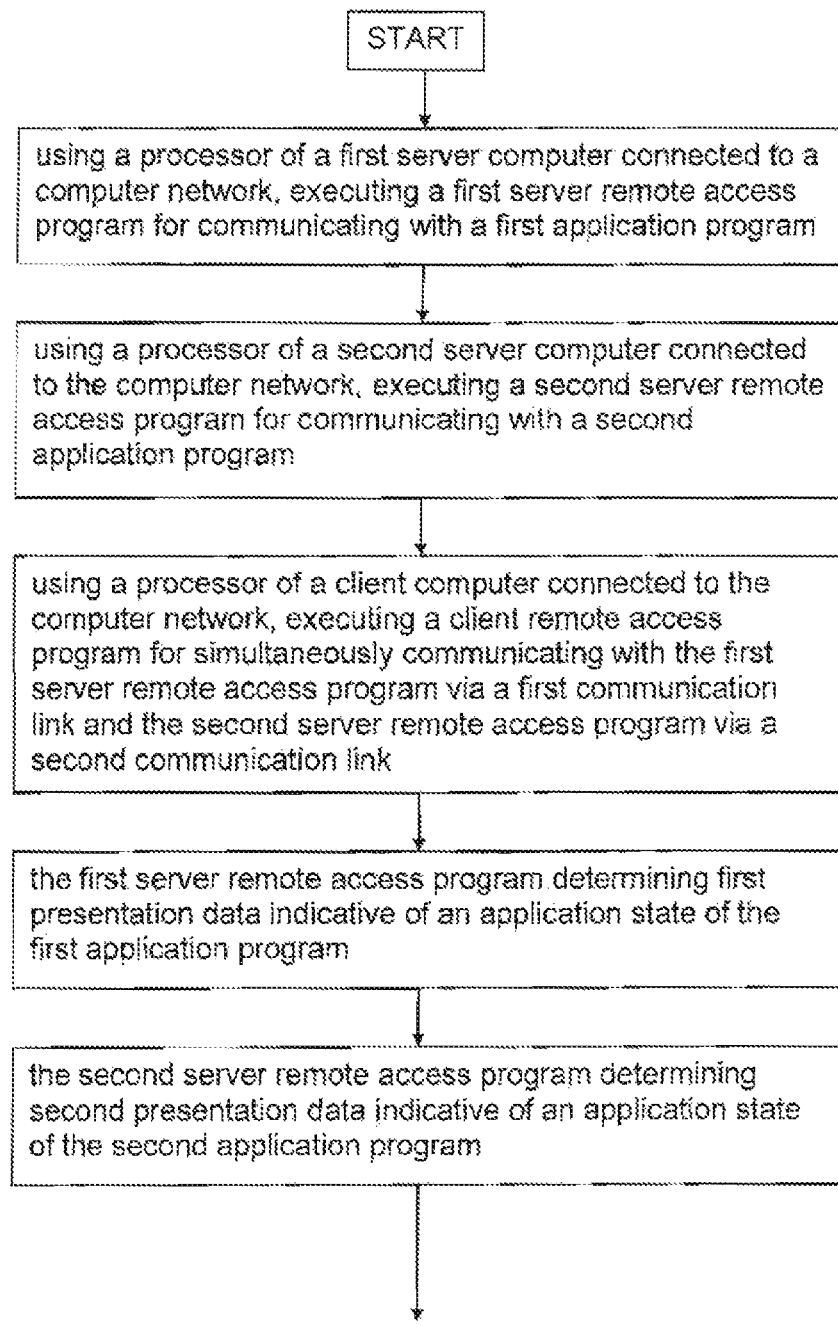
FIGS. 3a to 3c are simplified flow diagrams of a method for providing remote access to data for display on a mobile device via a computer network.
Figure 3A:
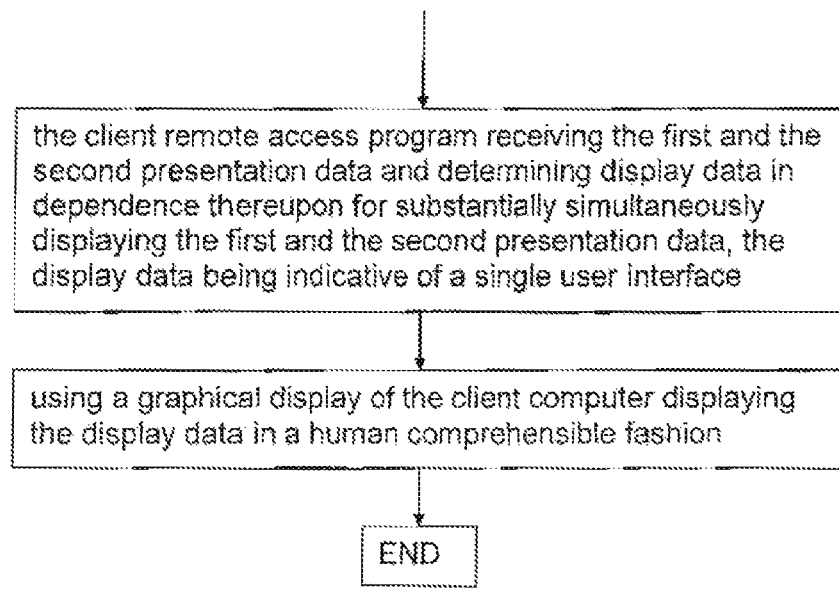

Referring to FIG. 3a, a method for providing remote access to data for display on a client computer via a computer network is shown. Using the processor 104A of the first server computer 102A connected to the computer networks 109A and 110, a first server remote access program for communicating with the first application program is executed (10). Using the processor 104B of the second server computer 102B connected to the computer networks 109B and 110, a second server remote access program for communicating with the second application program is executed (12). Using the processor 118A, 118B of the client computer 112A, 112B connected to the computer network 110, a client remote access program is executed (14) for simultaneously communicating with the first server remote access program via a first communication link—computer networks 110 and 109A—and the second server remote access program via a second communication link—computer networks 110 and 109 A. The first server remote access program determines (16) first presentation data indicative of an application state of the first application program. For example, the first server remote access program receives image data from the first application program such as a PACS program and determines first presentation data in dependence thereupon.

Optionally, at 14, the client remote access program may provide a mechanism for a single sign-on at the first server remote access program and second server remote access program to authenticate a user of the client computer with both the first server computer and second server computer. As such, the user may not be required to separately authenticate with each of the first server computer and the second server computer.

The second server remote access program determines (18) second presentation data indicative of an application state of the second application program. Preferably, the steps 16 and 18 are performed in a substantially simultaneous fashion. The client remote access program receives the first and the second presentation data and determining (20) display data in dependence thereupon for substantially simultaneously displaying the first and the second presentation data. The display data may be indicative of a single user interface as will be described herein below. Using the graphical display 114A, 114B of the client computer 112A, 112B the display data are displayed (22) in a human comprehensible fashion.

Figure 3B:
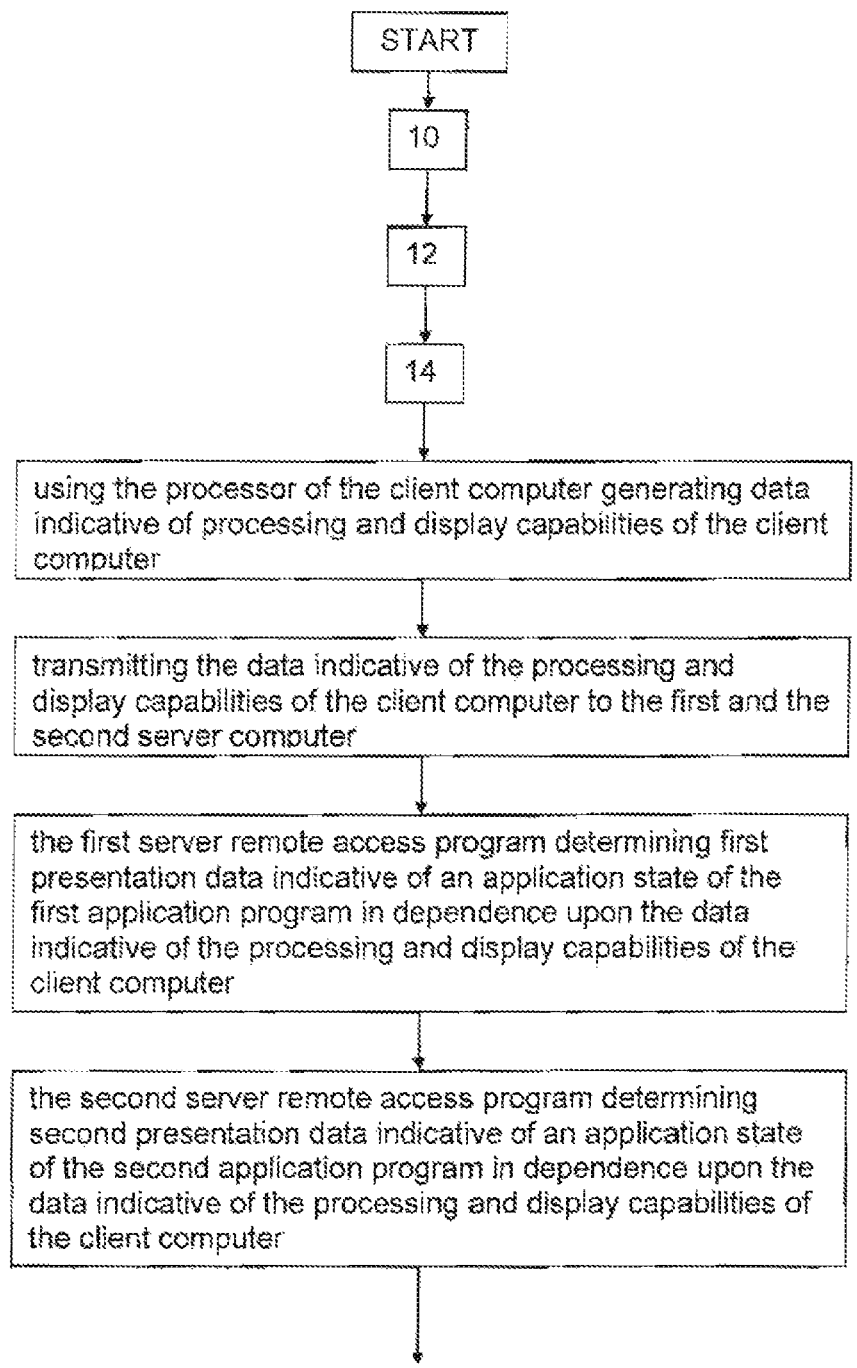
Figure 3B:
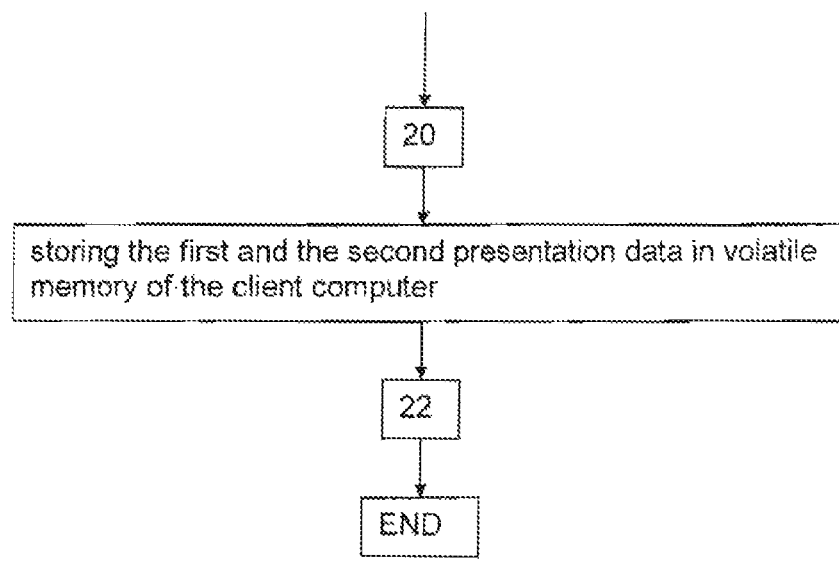

Referring to FIG. 3b, a method for providing remote access to data for display on a client computer via a computer network is shown. The method illustrated in FIG. 3b comprises the same structure as the method illustrated in FIG. 3a with same reference numerals indicating same steps. The method comprises additional steps interposed after step 14. At 30, the processor 118A, 118B of the client computer 112A, 112B generates data indicative of the processing and display capabilities of the client computer 112A, 112B and transmits the same (32) to the first and the second server remote access program executed on the first and second server computer. The first server remote access program then determines (16A) first presentation data indicative of an application state of the first application program in dependence upon the data indicative of the processing and display capabilities of the client computer. For example, the first server remote access program receives image data from the first application program such as a PACS program and determines first presentation data in dependence thereupon. The presentation data are then generated in dependence upon the previously received data indicative of the processing and display capabilities such as, for example, processing capacity, volatile memory size, type and size of graphical display, and type of user interface, of the client computer 112A, 112B, such as an IPHONE, a BLACKBERRY, a desktop computer, a laptop/notebook computer, etc. The second server remote access program may determine substantially simultaneously (18A) second presentation data indicative of an application state of the second application program in dependence upon the data indicative of the processing and display capabilities of the client computer 112A, 112B.

Optionally, after receipt of the first and second presentation data (20) the processor 118A, 118B stores (34) the first and second presentation data in volatile memory of the client computer 112A, 112B, for example, until the present communication with the first and the second server computer 102A and 102B is terminated.

For example, the steps 30 and 32 are performed during initiation of the communication with the first and the second server remote access program, Using the processor 118A, 118B of the client computer 112A, 112B first request data indicative of a first request for provision of data indicative of the state of the first application program are generated, Using the processor 118A, 118B of the client computer 112A, 112B second request data indicative of a second request for provision of data indicative of the state of the second application program are generated. Preferably, the request data comprise data indicative of the processing and display capabilities of the client computer 112A, 112B. The first request data are then transmitted to the first sever computer 102A and the second request data are transmitted to the second server computer 102B, preferably, in a substantially simultaneous fashion.

Referring to FIGS. 3c and 4a to 4c, a method for providing remote access to data for display on a client computer via a computer network is shown. The method illustrated in FIG. 3c comprises the same structure as the method illustrated in FIGS. 3a and 3b with same reference numerals indicating same steps. The method comprises additional steps interposed after step 14. At 40, the processor 118A, 118B of the client computer 112A, 112B associates interactive functionalities of the first and the second application program with respective interaction zones 204, 304. Preferably, an interactive functionality being a same in both application programs is associated with a single interaction zone. Using the processor 118A, 118B of the client computer 112A, 112B, display data indicative of the interaction zones are generated (42). The interaction zones enable user interaction with the first and the second application program. The 118A, 118B of the client computer 112A, 112B receives (44) user input data, for example, from the touch screen 114A, determines (46) an association of the received user input data to a respective interaction zone, and provides (48) the user input data to the application program associated with the respective interaction zone.

Optionally, the user input data are simultaneously provided to the first and the second application program if associated with a single interaction zone.

Further optionally, the interaction zones may not correspond to a physical display, but are associated with off-screen display buffers with sizes, color, depth, and resolution that are independent of hardware capabilities of the server computer and the client computer. The server computer then sizes the interaction zones to match each client, for example, in a round robin fashion as each connected client is updated. Alternatively, one size is used for all clients and the server computer sends interaction zone scaling instructions to each client computer for display.

Figure 3C:
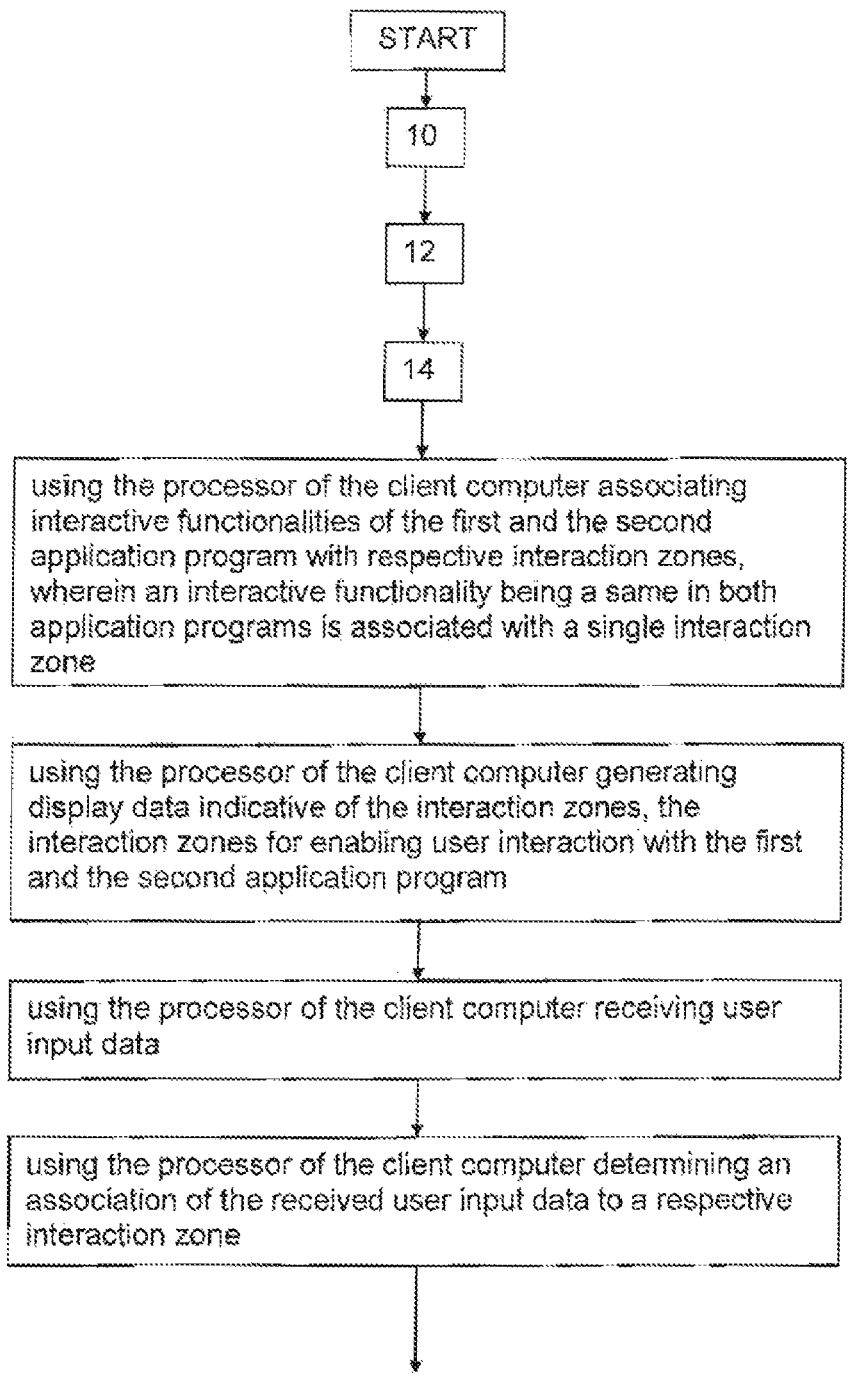
Figure 3C:
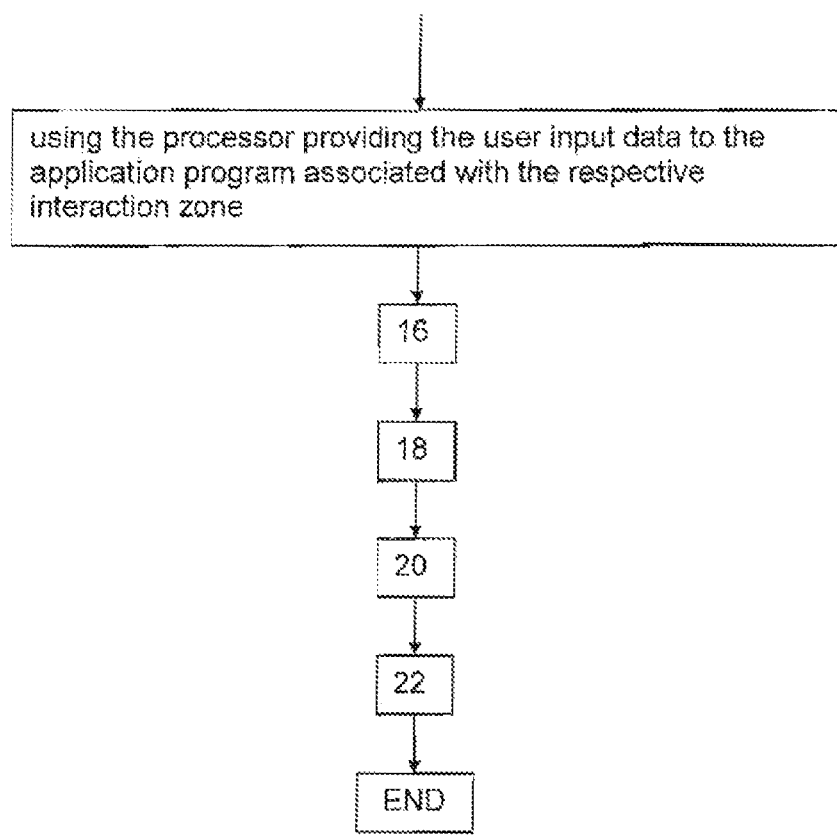

The method illustrated in FIG. 3c facilitates user interaction with the application programs for, for example, zooming into a Region of Interest (ROI) in the image data, changing a view in 3D images, or performing image rendering processes.

Figure 4A:
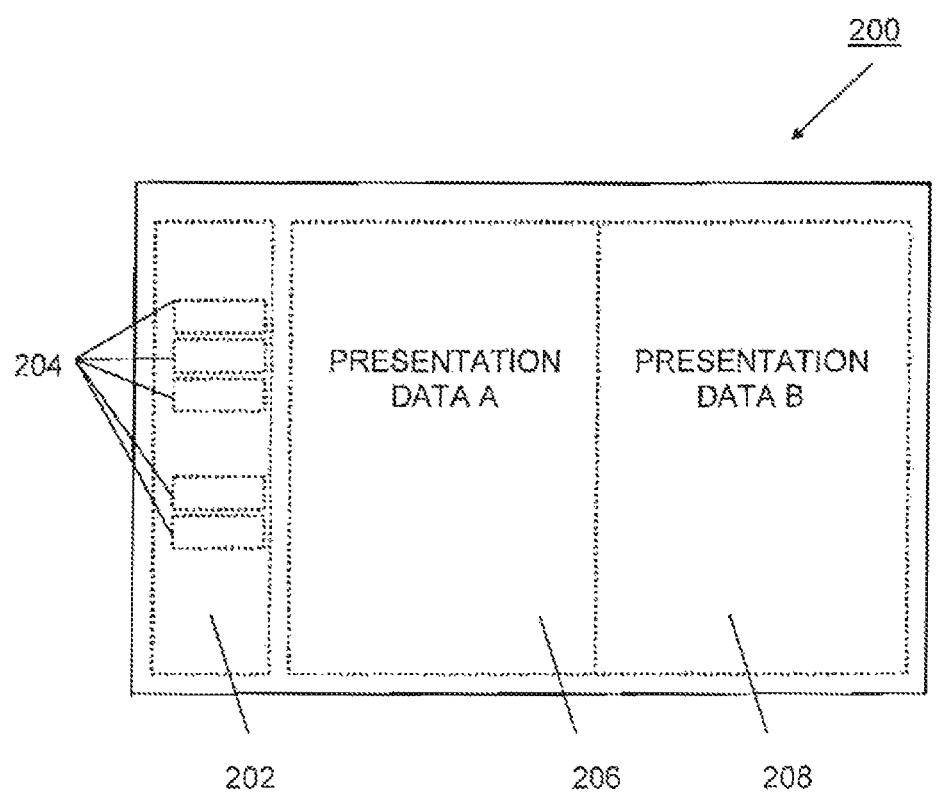
FIGS. 4a to 4c are simplified block diagrams illustrating displays for displaying the first and the second presentation data in a single user interface for use in the method illustrated in FIGS. 3a to 3c.
Figure 4B:
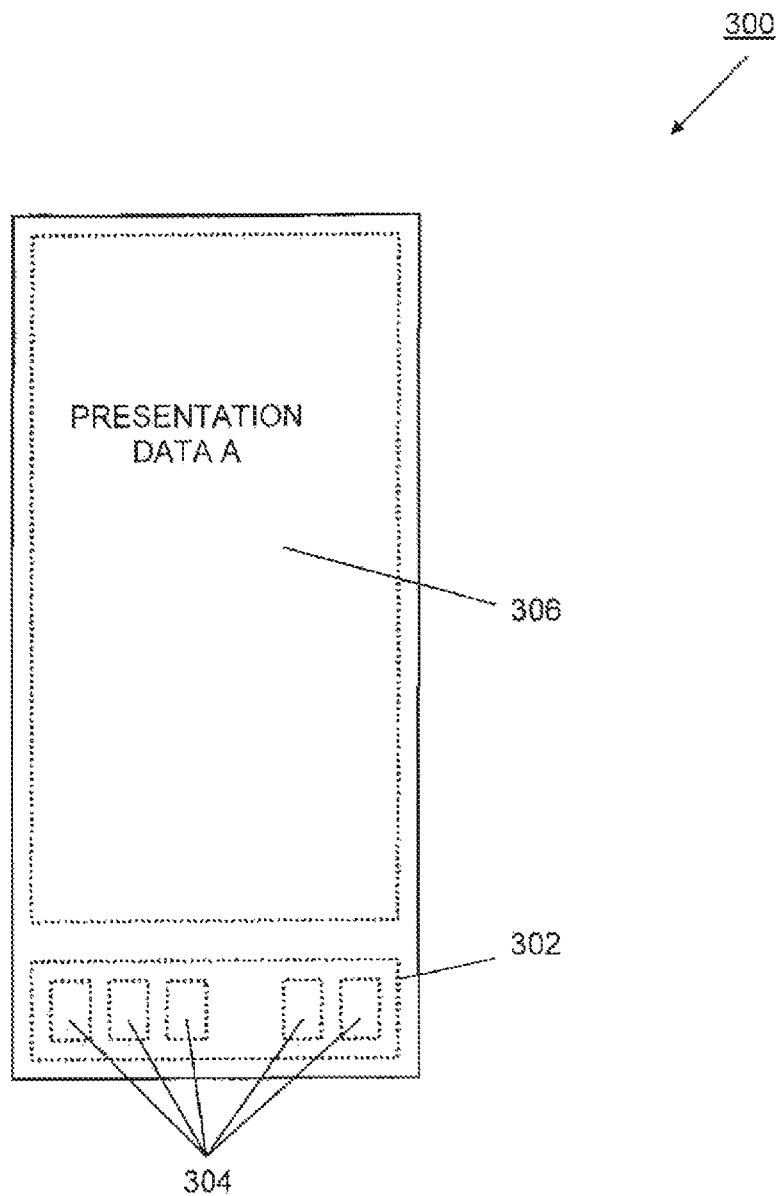
Figure 4C:
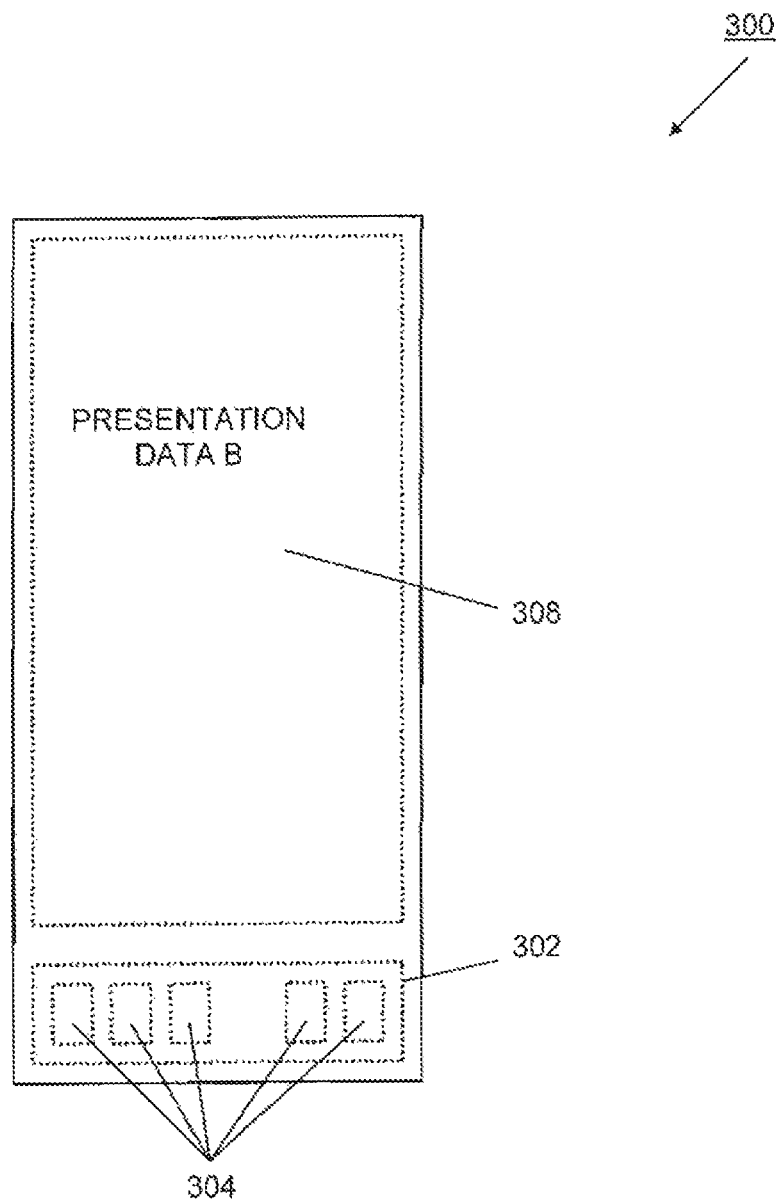

FIGS. 4a to 4c illustrate examples of displays for displaying the first and the second presentation data in a single user interface. The single user interface 200, illustrated in FIG. 4a, comprises two image display fields 206 and 208 for simultaneously displaying the first and the second presentation data, for example, in a side by side fashion. The interaction zones 204 are displayed in an interaction field 202 placed, for example, to the left hand side of the image display field 206. Other display options include placing: the display fields 206 and 208 on top of each other; the interaction field in different locations on the screen; the interaction zones in a plurality of different locations on the screen. Optionally, the user of the client computer 112A, 112B is enabled to place the various fields and/or interaction zones using, for example, drag and drop technology.

The single user interface 300, illustrated in FIGS. 4b and 4c, comprises one image display field 306 or 308 displayed in FIGS. 4b and 4c, respectively, for substantially simultaneously displaying the first and the second presentation data by flipping between the display fields 306 and 308. Each display field 306 and 308 is displayed together with the interaction zones 304 in interaction field 302. The single user interface 300 enables display of the presentation data on small displays of handheld wireless devices such as, for example, an IPHONE.

Of course, the methods for providing remote access to data for display on a client computing via a computer network according to the present disclosure is not limited to the computer network architecture illustrated in FIGS. 1 and 2. For example, the LANs 109A, 109B may be omitted and the first and the second server computer 102A may be directly connected to the computer network 110 with the databases 108A and 108B being directly connected to the respective first and second server computers 102A, 102B.

The present disclosure has been described herein with regard various implementations. However, it will be obvious to persons skilled in the art that a number of variations and modifications can be made without departing from the scope of the disclosure as described herein.

What is claimed is:

1. A method of providing a split-screen user interface, comprising:
    displaying a single user interface within a physical display associated with a client computer, the single user interface comprising a first image display field and a second image display field;
    executing a client remote access program at the client computer that is associated with the single user interface;
    using the client remote access program to establish a first remote network connection between the client computer and a first server on which a first application program executes;
    using the client remote access program to establish a second remote network connection between the client computer and a second server on which a second application program executes using the client remote access program;
    receiving first presentation data associated with the first application program over the first remote network connection;
    receiving second presentation data associated with the second application program over the second remote network connection;
    displaying the first presentation data associated with the first application program in the first image display field, the first presentation data being generated in accordance with processing capabilities of the client computer;
    displaying the second presentation data associated with the second application program in the second image display field, the second presentation data being generated in accordance with processing capabilities of the client computer; and
    independently updating the first image display field and the second image display field in response to (1) execution of the first application program and the second application program or (2) user inputs received in the first image display field and the second image display field.

2. The method of claim 1, further comprising presenting the first image display field and the second image display field in either a side-by-side orientation or a top-and-bottom orientation.

3. The method of claim 1, further comprising presenting the single user interface in a web browser.

4. The method of claim 1, further comprising displaying an interaction field in the single user interface to enable user interaction with the first application program and the second application program.

5. The method of claim 4, further comprising displaying interaction zones within the interaction field, wherein each interaction zone provides a function associated with the first application program or the second application program to enable the user interaction.

6. The method of claim 4, further comprising sizing at least one of the first image display field, the second image display field, the interaction field or the interaction zones in accordance with a size of the physical display of the client computer.

7. The method of claim 1, further comprising zooming into a region of interest in either the first image display field or the second image display field in response to a user input.

8. The method of claim 1, wherein the first application program and the second application program are respectively executed on a first server computer and a second server computer.

9. The method of claim 8, further comprising:
    receiving, at the client remote access program executing on the client computer, the first presentation data from the first server computer, which represents a change in a state of the first application; and
    receiving, at the client remote access program executing on the client computer, the second presentation data from the second server computer, which represents a change in a state of the second application.

10. The method of claim 8, further comprising:
    receiving the user inputs from the first image display field at the client remote access program executing on the client computer;
    communicating the user inputs from the client remote access program to a first server remote access program executing on the first server computer;
    receiving the user inputs from the second image display field at the client remote access program executing on the client computer; and
    communicating the user inputs from the client remote access program to a second server remote access program executing on the second server computer.

11. The method of claim 1, further comprising providing a single sign-on mechanism using the client remote access program, whereby a user authenticates with both the first application program and the second application program using the single sign-on mechanism.

12. The method of claim 1, further comprising:
    displaying the single user interface within a second physical display associated with a second client computer;
    displaying first presentation data associated with the first application program in the first image display field;
    displaying second presentation data associated with the second application program in the second image display field; and
    independently updating the first image display field and the second image display field in the single user interface at the client computer and the second client computer in response to (1) execution of the first application program and the second application program or (2) user inputs received in the first image display field and the second image display field at either the client computer and the second client computer.

13. A method of providing a split-screen user interface on a client computer to remotely access a first application program and a second application program, comprising:
- executing a client remote access program at the client computer that establishes remote network connections between the client computer and a first server on which a first application program executes and a second server on which a second application program executes;
- displaying a single user interface within a physical display of the client computer that includes a first image display field and a second image display field, wherein the first image display field displays a first application program user interface, and wherein the second image display field displays a second application program user interface, wherein image data associated with the first application program user interface and the second application program user interface is generated in accordance with processing capabilities of the client computer and communicated over the remote network connections; and
- independently updating the first image display field and the second image display field in response to (1) execution of the first application program and the second application program or (2) user inputs received in the first image display field and the second image display field.

14. The method of claim 13, further comprising displaying an interaction field in the single user interface to enable user interaction with the first application program and the second application program.

15. The method of claim 14, further comprising displaying interaction zones within the interaction field, wherein each interaction zone provides a function associated with the first application program or the second application program to enable the user interaction.

16. The method of claim 14, further comprising sizing at least one of the first image display field, the second image display field, the interaction field or the interaction zones in accordance with a size of the physical display of the client computer.

17. The method of claim 13, further comprising:
- receiving the user inputs from the first image display field at a client remote access program executing on the client computer;
- communicating the user inputs from the client remote access program to a first server remote access program executing on the first server computer;
- receiving the user inputs from the second image display field at the client remote access program executing on the client computer; and
- communicating the user inputs from the client remote access program to a second server remote access program executing on the second server computer.

18. The method of claim 13, further comprising providing a single sign-on mechanism using the client remote access program, whereby a user authenticates with both the first application program and the second application program using the single sign-on mechanism.

19. The method of claim 13, further comprising:
- executing a second client remote access program at a second client computer that establishes second remote connections between the second client computer and the first server and the second server;
- displaying a second single user interface within a second physical display of the second client computer that includes the first image display field and the second image display field, wherein image data associated with the first application program user interface and the second application program user interface is received over the second remote connections; and
- independently updating the first image display field and the second image display field in response to (1) execution of the first application program and the second application program or (2) user inputs received in the first image display field and the second image display field at either the client computer or the second client computer.

20. The method of claim 13, further comprising providing each of the client computer and the second client computer simultaneous access to the first application program and the second application program.

* * * * *